US008781068B2

(12) United States Patent
Noda (10) Patent No.: US 8,781,068 B2
(45) Date of Patent: Jul. 15, 2014

(54) X-RAY IMAGE DIAGNOSING APPARATUS

(75) Inventor: Koji Noda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/554,128

(22) Filed: Jul. 20, 2012

(65) Prior Publication Data

US 2012/0281812 A1 Nov. 8, 2012

Related U.S. Application Data

(63) Continuation of application No. PCT/JP2012/002746, filed on Apr. 20, 2012.

(30) Foreign Application Priority Data

Apr. 22, 2011 (JP) ................................. 2011-095881

(51) Int. Cl.
*A61B 6/00* (2006.01)
(52) U.S. Cl.
USPC .............................................. 378/62; 378/19
(58) Field of Classification Search
CPC ...................................................... A61B 6/469
USPC .................................................................. 378/62
See application file for complete search history.

(56) References Cited

U.S. PATENT DOCUMENTS

| 6,285,739 B1 | 9/2001 | Rudin et al. | |
|---|---|---|---|
| 2008/0187095 A1* | 8/2008 | Boone et al. | 378/37 |
| 2009/0274271 A1* | 11/2009 | Pfister et al. | 378/62 |
| 2010/0027742 A1* | 2/2010 | Movassaghi et al. | 378/62 |
| 2010/0091946 A1* | 4/2010 | Proksa | 378/62 |

FOREIGN PATENT DOCUMENTS

JP 2010-201103 A 9/2010

OTHER PUBLICATIONS

International Search Report issued on May 10, 2012 for PCT/JP2012/002746 filed on Apr. 20, 2012 (with an English translation of categories).
International Written Opinion issued on May 10, 2012 for PCT/JP2012/002746 filed on Apr. 20, 2012.
International Preliminary Report on Patentability and Written Opinion issued Oct. 31, 2013, in International Application No. PCT/JP2012/002746.

* cited by examiner

*Primary Examiner* — Hoon Song
*Assistant Examiner* — Danielle Fox
(74) *Attorney, Agent, or Firm* — Oblon, Spivak, McClelland, Maier & Neustadt, L.L.P.

(57) ABSTRACT

An embodiment includes an X-ray detecting section including an X-ray detector having a first visual field size and a high-resolution detector and having a second visual field size, an X-ray generating section for irradiating a subject with X-rays, an image processing section for generating a first X-ray image by means of the X-ray detector and a second X-ray image, a display section, a region defining section for displaying a spot corresponding to part of the second X-ray image or a region corresponding to the second X-ray image on the first X-ray image and specifying the position of the high-resolution detector by moving the spot or the region, a positional displacement calculating section for determining the coordinate difference between the center position of the first X-ray image and the position of the spot indicating the specified position and a move control section for controlling the top plate or the holding section.

15 Claims, 8 Drawing Sheets

X-RAY IMAGE DIAGNOSING APPARATUS

CROSS-REFERENCE TO RELATED APPLICATION

This application is a continuation of International Application No. PCT/JP2012/002746, filed on Apr. 20, 2012, which is based upon and claims the benefit of priority from the prior Japanese Patent application No. 2011-095881, filed on Apr. 22, 2011, the entire contents of which are incorporated herein by reference.

FIELD

Embodiments of the present invention relate to an X-ray image diagnosing apparatus.

BACKGROUND

In known X-ray image diagnosing apparatus having a C-arm type holder unit, an X-ray generating section and an X-ray detecting section are arranged at the respective opposite ends of the C-arm. A transparent image and a photographic image are displayed on a display monitor as a function of the dimensions of the X-ray detector (I.I: image intensifier or FPD: flat panel detector) and the values specified for visual field size.

In recent years, efforts have been paid to raise the level of diagnosis and therapeutic manual procedures by arranging a compact high-resolution X-ray detector in addition to an ordinary X-ray detector that provides an image size of about 8 to 16 inches in order to obtain a clearer image of a region of interest (ROI) such as a morbid area.

Apparatus having two X-ray detectors includes those having a switching arm mechanism disposed in the X-ray detecting section of the apparatus to place, when necessary, the compact high-resolution detector in front of the ordinary visual field size X-ray detector to collect high-resolution images but, when not necessary, retract the high-resolution detector.

The switching arm mechanism of this configuration is arranged so as to make the center of the image obtained by means of the ordinary X-ray detector agree with center of the image obtained by means of the compact high-resolution detector and the images obtained by means of the two detectors agree with the center of the focus of X-rays.

With an X-ray image diagnosing apparatus equipped with a compact high-resolution detector having a small visual field, the visual field becomes small as the ordinary X-ray detector is switched to the compact high-resolution detector. Thus, either the ROI needs to be aligned with the image center before selecting the small visual field or, after selecting the small visual field, the C-arm needs to be driven or the bed needs to be moved for an adjustment operation of putting the ROI into the small visual field. This gives rise to a problem of making the system rather inconvenient and the therapeutic manual procedures inefficient.

Figure 11:
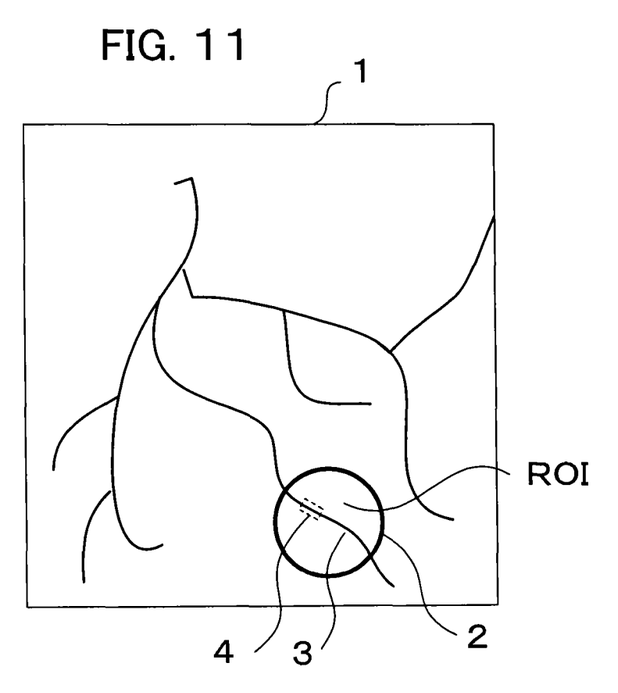
FIG. 11 is a schematic illustration of an exemplar display image formed by a known X-ray image diagnosing apparatus having two X-ray detectors.

On the other hand, there are known X-ray image diagnosing apparatus having two X-ray detectors of the type where the operator of such an X-ray image diagnosing apparatus specifies the spot he or she wants to look at in detail, for example, the position where a stent 4 is buried in a blood vessel 3, on X-ray image 1 obtained by means of the ordinary X-ray detector by means of a marker 2 so as to make the spot includes the ROI.

Then, only the compact high-resolution detector is moved according to the coordinate data of the specified marker (ROI) and the whole image is displayed, including the ROI part that is displayed as a high-resolution image. However, with such an X-ray image diagnosing apparatus, the ROI image can be displayed at a side position in the displayed whole image to make it inconvenient for image diagnosis.

In such an instance, the operator is required to carry out an additional operation of making the ROI part displayed at the center of the whole X-ray image. Furthermore, from the structural point of view, a complex switching arm mechanism is required for such an operation because it needs to have an independent drive mechanism for moving only the compact high-resolution detector.

Therefore, the object of the present invention is to dissolve the above-identified problems and provide an X-ray image diagnosing apparatus that can carry out an examination operation promptly if a compact high-resolution detector having a small visual field is employed in it.

DETAILED DESCRIPTION

An X-ray image diagnosing apparatus according to an embodiment includes:

a top plate for laying a subject to be examined;

an X-ray detecting section including an X-ray detector having a first visual field size and a high-resolution detector showing a resolution higher than the X-ray detector and having a second visual field size smaller than the visual field of the X-ray detector;

an X-ray generating section for irradiating the subject with X-rays;

a holding section for holding the X-ray detecting section and the X-ray generating section so as to make them face each other;

an image processing section for generating a first X-ray image by means of the X-ray detector and a second X-ray image by means of the high-resolution detector;

a display section for displaying the first X-ray image and the second X-ray image;

a region defining section for displaying a spot corresponding to part of the second X-ray image or a region corresponding to the second X-ray image on the first X-ray image and specifying the position of the high-resolution detector by moving the spot or the region;

a positional displacement calculating section for determining the coordinate difference between the center position of the first X-ray image and the position of the spot indicating the specified position of the high-resolution detector or a substantial center position of the region; and a move control section for controlling the top plate or the holding section so as to move the substantial center position of the second X-ray image to a substantial center of the image display region of the display section.

Now, embodiments of the present invention will be described in detail below by referring to FIGS. 1 through 10.

First Embodiment

Figure 1:
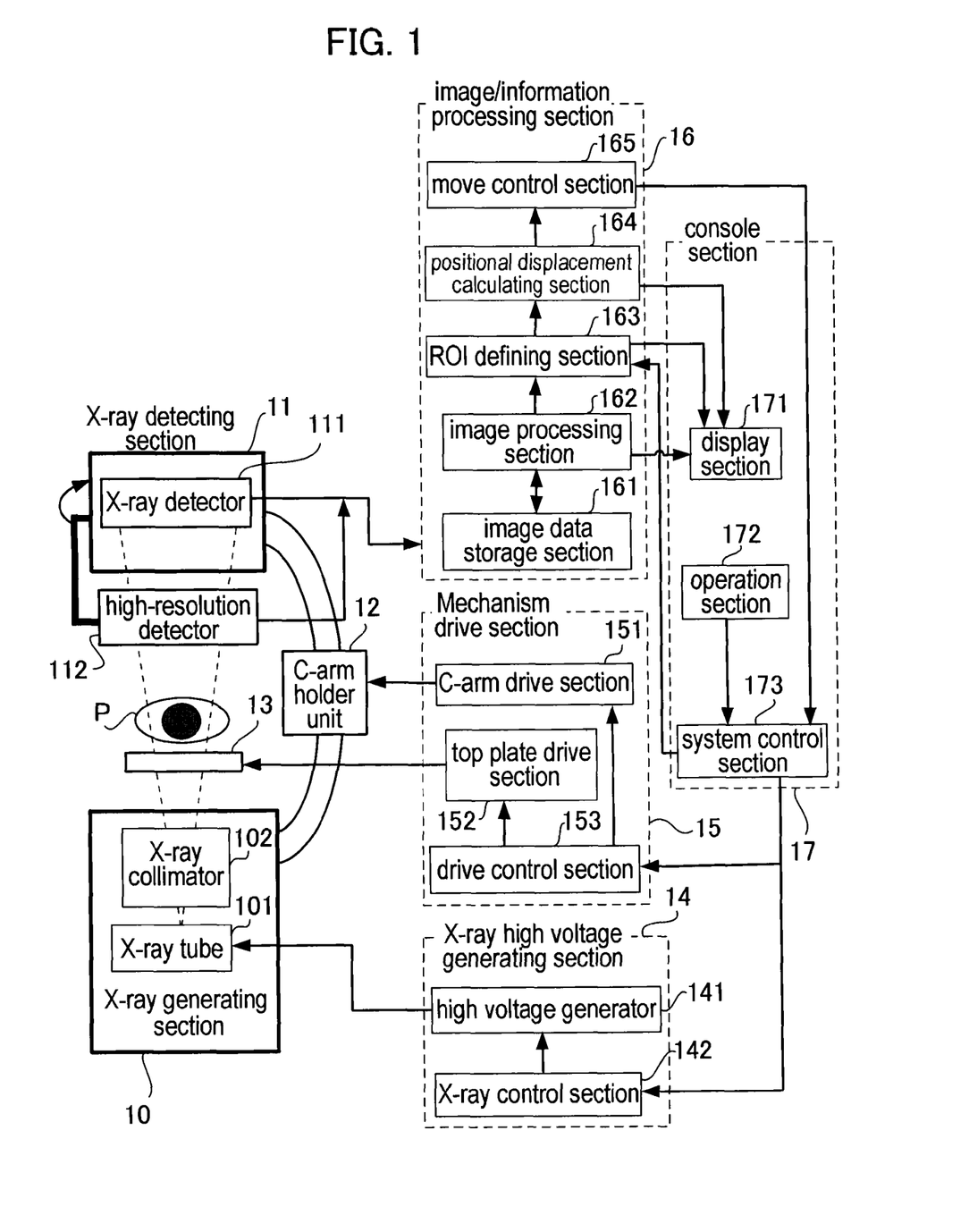
FIG. 1 is a schematic block diagram of an X-ray image diagnosing apparatus according to a first embodiment of the present invention.
Figure 2:
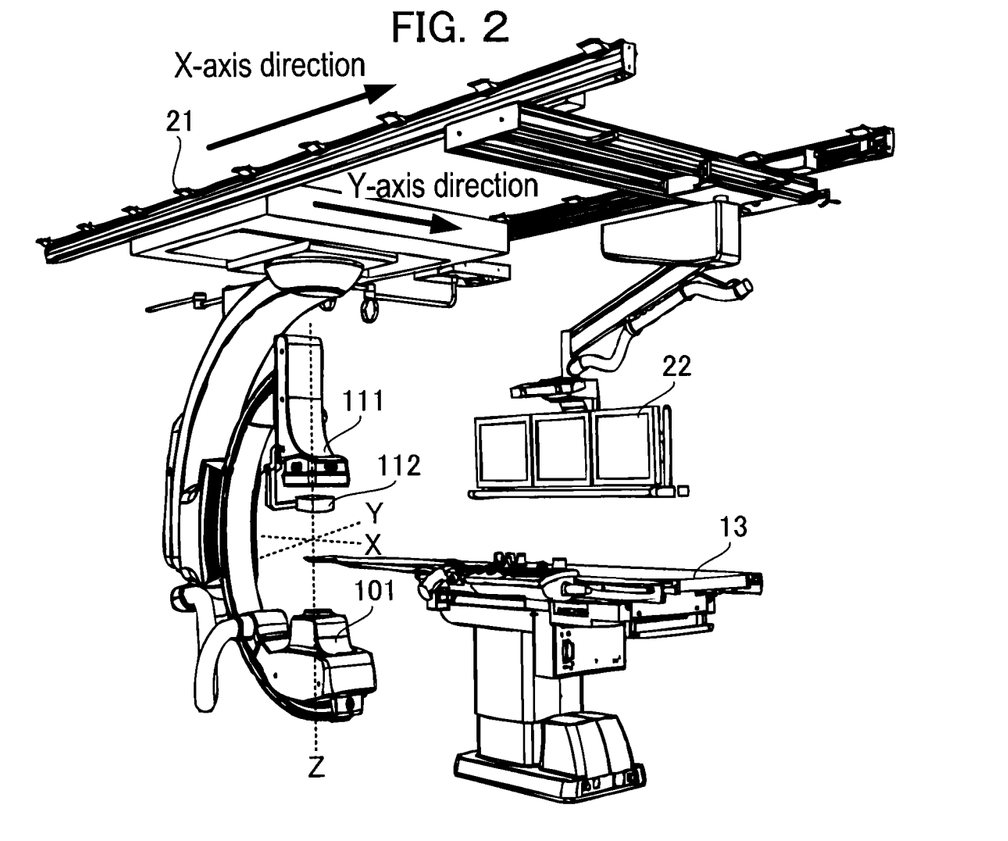
FIG. 2 is a schematic perspective view of the ceiling-traveling type C-arm holder unit of the X-ray image diagnosing apparatus according to the first embodiment, illustrating the configuration thereof.
Figure 3:
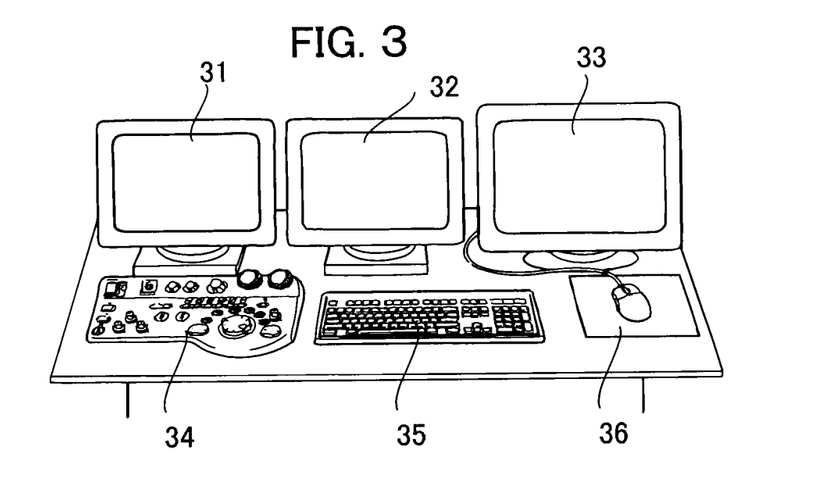
FIG. 3 is a schematic view of an exemplar console that can be used for the first embodiment.

The embodiments of X-ray image diagnosing apparatus that will be described below includes a C-arm that has an X-ray generating section and an X-ray detecting section and is capable of freely rotating. Firstly, the configuration of the X-ray image diagnosing apparatus will be described by referring to FIGS. 1 through 3. FIG. 1 is a schematic block diagram of the X-ray image diagnosing apparatus, illustrating the overall configuration thereof. FIG. 2 is a schematic illustration of the configuration of the X-ray image diagnosing apparatus having a ceiling-traveling type C-arm holder unit. FIG. 3 is a schematic illustration of the configuration of the console section thereof.

The X-ray image diagnosing apparatus of this embodiment includes a C-arm and includes an X-ray generating section 10 for irradiating subject P to be examined with X-rays, an X-ray detecting section 11 for two-dimensionally detecting X-rays being transmitted through the subject P, a C-arm holder unit 12 for holding the X-ray generating section 10 and the X-ray detecting section 11, a bed for laying a subject P and an X-ray high voltage generating section 14 for generating a high voltage required to irradiate X-rays from the X-ray generating section 10.

The X-ray image diagnosing apparatus further includes a mechanism drive section 15 for controlling the position and the rotary motion of the C-arm that is held by the C-arm holder unit 12 and also controlling the move of the bed 13, an image/information processing section 16 for generating and storing X-ray image data according to the projected data of the subject P as detected by the X-ray detecting section 11 and executing various arithmetic operations and a console section 17 for operating and controlling the X-ray image diagnosing apparatus and displaying various images.

The X-ray generating section 10 includes an X-ray tube 101 for irradiating the subject P with X-rays and an X-ray collimator 102 for forming an X-ray cone beam out of the X-rays irradiated from the X-ray tube 101. The X-ray tube 101 is a vacuum tube for generating X-rays and generates X-rays by applying a high voltage to thermal electrons emitted from a cathode (filament) to accelerate them and causing the accelerated thermal electrons to collide with a tungsten anode.

On the other hand, the X-ray collimator 102 is arranged between the X-ray tube 101 and the subject P and has a function of condensing the X-rays irradiated from the X-ray tube 101 to a predetermined irradiation size. In this embodiment in which the X-ray detecting section 11 includes a plurality of X-ray detectors, when one of the X-ray detectors is selected for operation, the irradiated X-rays are automatically condensed to an irradiation size that corresponds to the size of the visual field of the X-ray detector.

The X-ray detecting section 11 includes a flat X-ray detector 111 (FPD) adapted to transform the X-rays transmitted through the subject P into an electric charge and accumulate such electric charges and a high-resolution detector 112. While the high-resolution detector 112 is a sort of X-ray detector adapted to transform X-rays into an electric charge and accumulate electric charges, it can acquire an image of a part of the site of X-ray irradiation of the subject P observed by the FPD with higher resolution. The high-resolution detector 112 is supported typically by an arm and provided with a switching mechanism so that it can be placed in front of the X-ray detector 11 whenever necessary but it can be drawn away to a retreat position when it is not in use.

Although not shown in the drawings, the X-ray detecting section 11 also includes a projection data generating section for reading out the electric charges accumulated in the X-ray detector 111 and the high-resolution detector 112 and generating X-ray projection data from the read out electric charges.

The X-ray detector 111 is typically formed by using an FPD. The panel sizes of FPDs are normally 8-16 inches except specially designed ones. An FPD is formed by two-dimensionally arranging minute detection elements in column and row directions. Each detection element is formed by a photoelectric membrane that detects X-rays and generates an electric charge according to the quantity of incident X-rays, a charge storage capacitor that stores the electric charge generated by the photoelectric membrane and a TFT (thin film transistor) that reads out the electric charge stored in the charge storage capacitor at predetermined timings.

The high-resolution detector 112 provides high-resolution if compared with a FPD but has a narrow visual field. Its visual field is, for example, circular with a diameter of about 20 to 30 mm, rectangular or square. The high-resolution detector 112 is formed typically by forming a scintillator on a CCD (charge coupled device) that is formed on a single crystal Si substrate. Since the visual field size of a high-resolution detector is determined by the size of the Si substrate, it is difficult to prepare a high-resolution detector having a large area.

The X-ray high voltage generating section 14 includes a high voltage generator 141 for generating a high voltage to be applied between the anode and the cathode of the X-ray tube 101 in order to accelerate the thermal electrons generated from the cathode and an X-ray control section 142 for controlling the tube current, the tube voltage and the X-ray irradiation conditions such as the duration of irradiation at the high voltage generator 141 according to a directive signal from a system control section 173.

The mechanism drive section 15 includes a C-arm drive section 151 for supplying drive signals to a slide mechanism, a rotary mechanism and a move mechanism arranged at the C-arm holder unit 12, a top plate drive section 152 for supplying a drive signal for longitudinally and transversally driving the top plate of the bed 13, and a drive control section 153 for controlling the C-arm drive section 151 and the top plate drive section 152.

The image/information processing section 16 includes an image data storage section 161 for temporarily or permanently storing image data such as projection data of the X-ray detector 111, an image processing section 162 for acquiring desired image data from the image data storage section 161 and performing various image processing operations such as operations of generating 3D angio images, a ROI (region of interest) defining section 163 for defining a ROI for a high-resolution observation, a positional displacement calculating section 164 for calculating the positional difference between the center of the region whose coordinates are defined by the ROI defining section 163 and the center of the image obtained by means of the X-ray detector 111 and a move control section 165 for driving the C-arm or the top plate of the bed according to the numerical values obtained as a result of calculations by the positional displacement calculating section 164 and controlling the move of the C-arm or the top plate, whichever appropriate, so as to make the center of the ROI agree with the center of the image obtained by means of the X-ray detector 111.

Thus, the move control section 165 controls the operation of moving the C-arm or the top plate of the bed 13 in this way and consequently the high-resolution detector 112 automatically moves to the position in front of the X-ray detector from the retreat position in an interlocked manner. Therefore, a high-resolution image centered at the ROI is displayed substantially at the center of the whole image.

An exemplar configuration of the ceiling-traveling type C-arm holder unit will be described below by referring to FIG. 2. A rail 21 along which the ceiling-traveling type C-arm is driven to move is arranged under the ceiling and the C-arm holder unit 12 is suspended from the rail 21 and driven to travel. Assume that the traveling direction (the direction of the rail) extends in the direction of X-axis. Also assume that the C-arm holder unit 12 is equipped with a mechanism that drives the C-arm in a direction perpendicular to the rail, or in the direction of Y-axis.

Additionally, assume that the longitudinal direction of the bed 13 agrees with the direction of X-axis for the purpose of simplicity of explanation and the transversal direction of the bed 13 agrees with the direction of Y-axis. As shown in FIG. 2, a display monitor 22 is arranged in the examination chamber to display medical images apart from the console section 17, which will be described hereinafter by referring to FIG. 3.

The console section 17 shown in FIG. 1 is normally arranged in an operation chamber and equipped with a display section 171 for displaying desired image data selected from the image data stored in the image/information processing section 16. It also includes an operation section 172 for selecting and specifying various conditions including information on the subject, imaging sequence conditions, display conditions and X-ray irradiation conditions and for inputting various commands, and a system control section 173 for collectively controlling the units of the X-ray image diagnosing apparatus.

As shown in FIG. 3, the display section 171 is equipped with a fluoroscopic monitor 31 for displaying various image data generated in the image/information processing section 16, a reference monitor 32 for defining ROIs and displaying images of other modalities and a system monitor 33 for inputting imaging conditions and displaying various input/specification images for controlling the system.

The operation section 172 is equipped with input devices including a main console 34 having one or more track balls, one or more joysticks and various buttons, a keyboard 35 and a mouse 36 along with one or more foot switches (not shown). Information on the subject can be input and X-ray irradiation conditions and an image magnification can be selected and specified by way of these input interfaces. The input interfaces can also be used to select an imaging sequence such as a "rotating" imaging sequence, to specify the position and direction of imaging and to input various commands such as an imaging start command.

The system control section 173 is provided with a CPU and a memory circuit (not shown), and temporarily stores information for controlling the apparatus, command signals input by the operator from the operation section 172 and information on various initialization conditions and collectively controls the units of the X-ray image diagnosing apparatus.

Figure 4:
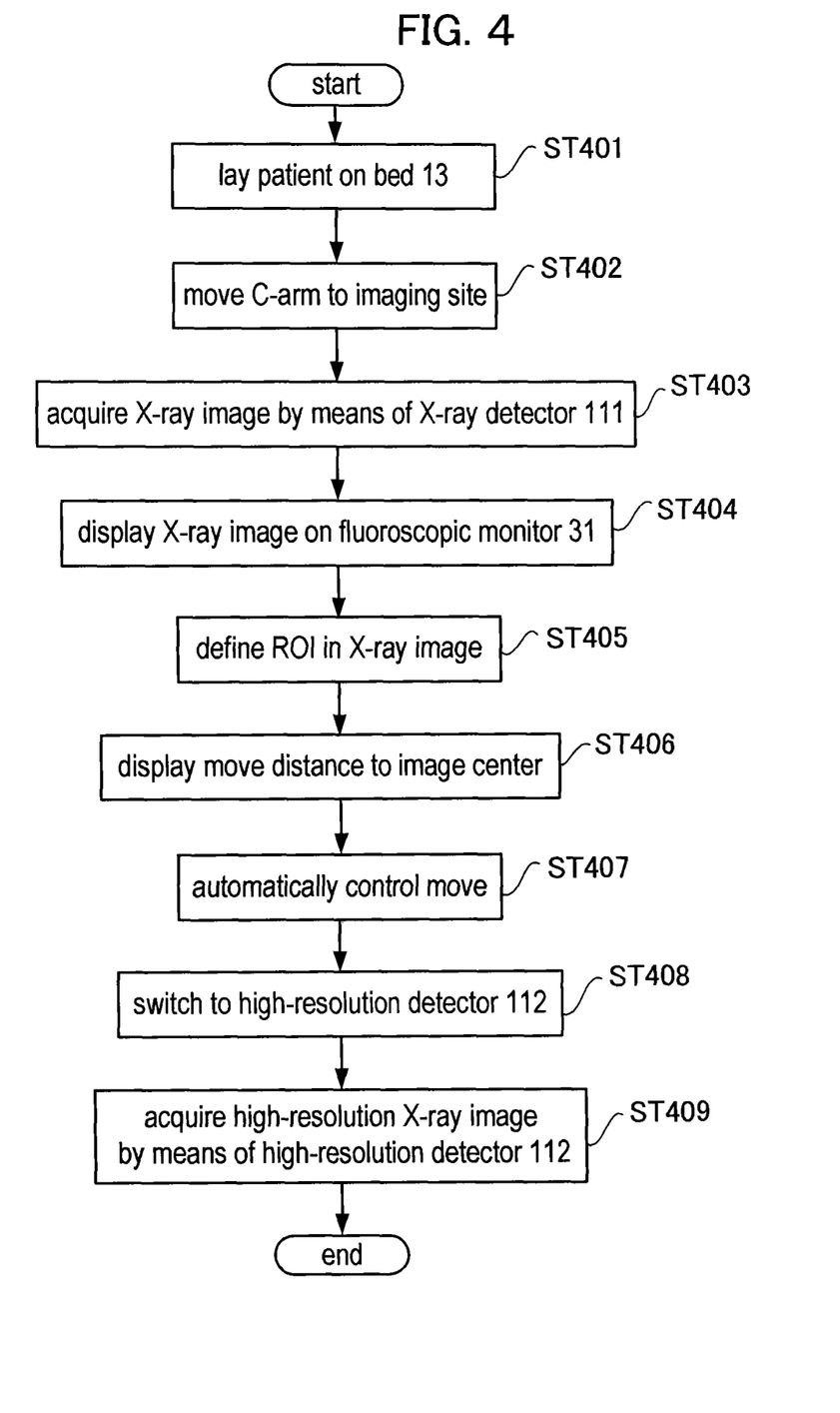
FIG. 4 is a flowchart of the operation of the high-resolution detector of the first embodiment.

Now, the processing operation for using the high-resolution detector 112 will be described below by referring to the flowchart of FIG. 4. Firstly, in Step ST401, the subject P (patient) is made to lie flat on the bed 13. In the next step, or Step ST402, the operator adjusts the height and the position of the top plate of the bed 13 and moves the C-arm to imaging site. The C-arm can be moved by using the console section 17 and controlling the C-arm holder unit 12 from the system control section 173 by way of the drive control section 153.

The imaging site is moved to the isocenter of the C-arm and, in Step ST403, a directive is issued at the console section 17 to acquire an X-ray image, using the X-ray detector 111 having an ordinary visual field. At this time, the high-resolution detector 112 is drawn away from the front side of the X-ray detector 111.

In Step ST404, the system control section 173 causes the X-ray generating section 10 to emit X-rays toward the subject P according to the imaging conditions and the operation instruction given to it. Then, the X-ray detecting section 11 temporarily stores the detected projection data and the image processing section 162 generates an X-ray image and displays it on the fluoroscopic monitor 31.

In Step ST405, the X-ray image same as the one being displayed on the fluoroscopic monitor 31 is displayed on the reference monitor 32 and the ROI to be displayed and observed by means of the high-resolution detector 112 is defined.

Figure 5:
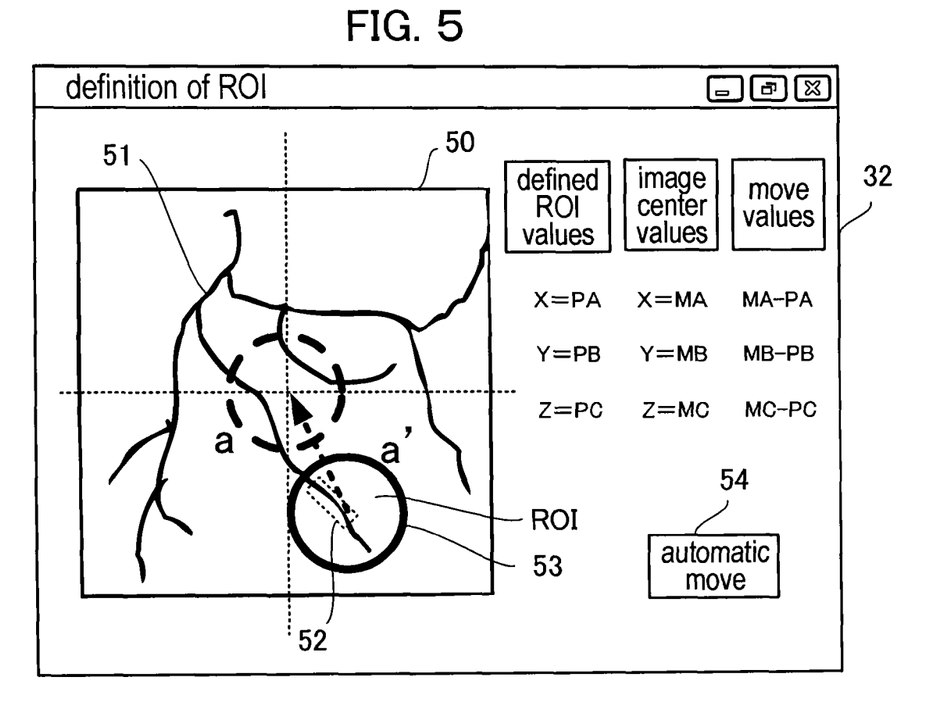
FIG. 5 is a schematic illustration of defining a ROI in the first embodiment.
Figure 6:
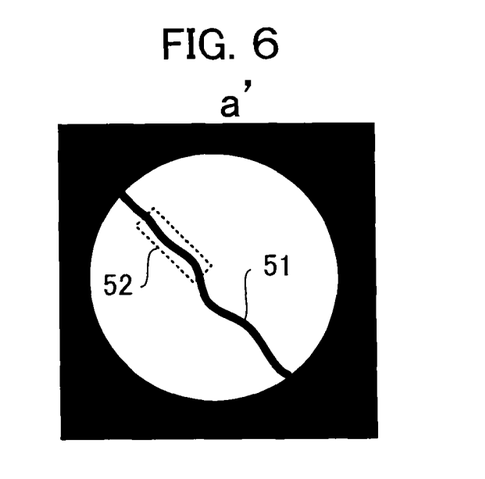
FIG. 6 is an exemplar transparent image obtained by means of the high-resolution detector of the first embodiment after defining a ROI.

FIG. 5 shows an exemplar X-ray image that can be displayed on the reference monitor 32. In this example, blood vessels 51 are being observed as X-ray image 50. If a stent 52 is buried in part of the blood vessels 51 as shown in FIG. 6, the conditions of the stent 52 cannot be observed in detail with the magnifications of the X-ray detector 111 having an ordinary visual field.

Therefore, to observe the conditions in greater detail by means of the high-resolution detector 112, marker 53 is made to display the region that corresponds to the visual field of the high-resolution detector 112 on the X-ray image 50 obtained by means of the X-ray detector 111. Then, a ROI is defined typically by means of the mouse 36 of the console section 17 so as to make the marker 53 include the ROI. Instead of definition by the ROI, it is possible to specify a spot corresponding to part of the second X-ray image on the X-ray image 50.

In Step ST406, as a ROI is defined, the coordinate values of the center position of the marker 53 (ROI defining values: X=PA, Y=PB, Z=PC) and those of the center position of the X-ray image 50 (X=MA, Y=MB, Z=MC) are displayed typically at a right side position on the display screen of the reference monitor 32 along with the differences of the coordinate values of the two center positions (ΔX=MA−PA, ΔY=MB−PB, ΔZ=MC−PC). The differences of the coordinate values are calculated by the positional displacement calculating section 164 and the amount of move of the C-arm is determined on the basis of the differences of the coordinate values.

In Step ST407, an automatic move control operation is conducted to move the C-arm according to the determined amount of move of the C-arm. For example, the C-arm may be moved both in the direction of the X-axis and in the direction of the Y-axis as shown in FIG. 2 by depressing automatic move button 54 to realize the amount of move of the C-arm. The high-resolution detector 112 is shifted substantially to the center of the image in an interlocked manner. In FIG. 5, the ROI shown by a' shifts to the ROI shown by a.

The automatic move control operation includes displaying an image of the area defined by the marker 53 substantially at the center of the whole image. This means that the image obtained by means of the high-resolution detector 112 is shifted to the center of the whole image obtained by means of the X-ray detector 111 in an interlocked manner. In actuality, the center of the image obtained by means of the high-resolution detector 112 and that of the image obtained by means of the X-ray detector 111 are interlocked and made to agree with each other. Therefore, it is only necessary to move the X-ray detector 111.

In the case of rotational imaging, the height of the top plate (in the direction of the Z-axis) needs to be adjusted so as to make center of the ROI agree with the isocenter. When the subject (patient) is made to bear an endoscope and/or a catheter, the operation of controlling the height of the top plate can be manually performed as option for the sake of safety of the subject.

It is assumed in the above description that the center of the X-ray image 50 agrees with the isocenter. In other words, the isocenter is located at the center of the X-ray image.

In Step ST408, the high-resolution detector 112 is set in front of the X-ray detector 111 and an image switching operation is conducted. In Step ST409, an enlarged image of the ROI defined in Step ST405 is displayed on the fluoroscopic monitor 31 as shown in FIG. 6.

With the above-described first embodiment, a marker that corresponds to the small visual field of the high-resolution detector is displayed on an image of an ordinary size obtained by means of the X-ray detector 111 and an ROI can be defined by means of the marker. The first embodiment has a functional feature of causing the ceiling-traveling type C-arm holder unit to operate as automatic follower and shift its position so as to move the ROI position substantially to the center of the X-ray image. This eliminates all the manual operations conventionally required to select a compact high-resolution detector including a positioning operation or an operation of manually moving a ROI to the center of an image obtained by means of an X-ray detector 111. Thus, the first embodiment is very convenient for use and can be used to build a system having highly efficient manual procedures.

Additionally, this embodiment displays the direction (and the amount) of a move of its C-arm on a monitor before it starts an automatic follow-up operation. Thus, the operator is notified of the direction in which and the position to which the C-arm moves in advance. Then, any interference accident due to an unintended move of the C-arm can be prevented from taking place.

Second Embodiment

Figure 7:
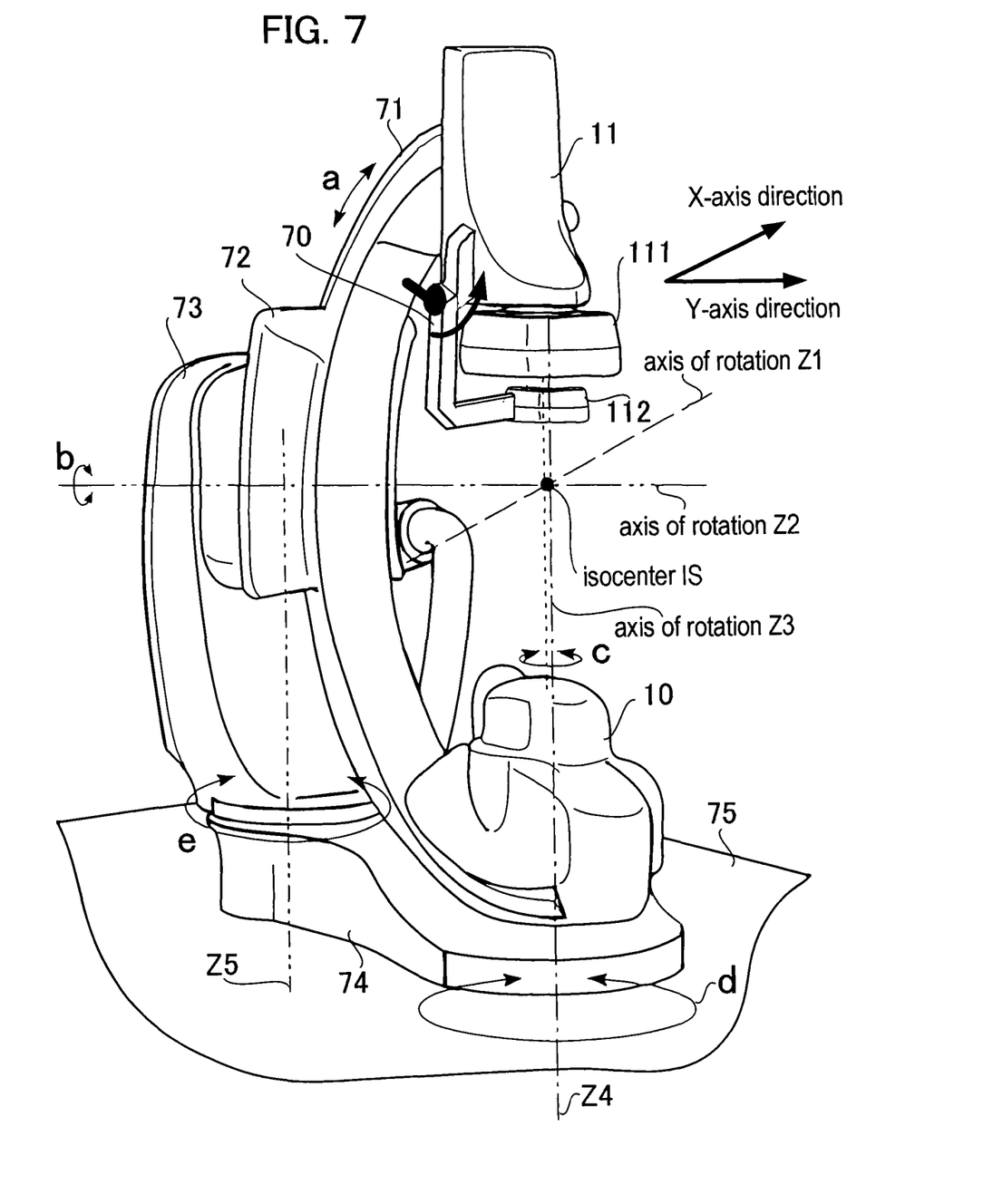
FIG. 7 is a schematic perspective view of the floor-standing five-axis C-arm holder unit of X-ray image diagnosing apparatus according to a second embodiment of the present invention, illustrating the configuration thereof.

An instance where a floor standing type five-axial C-arm holder unit is installed will be described below for this embodiment. The configuration of the X-ray image diagnosing apparatus of this embodiment is expressed by a block diagram that is same as that of FIG. 1. FIG. 7 illustrates the configuration of the floor standing type five-axial C-arm holder unit. Like the ceiling-traveling type C-arm holder unit shown in FIG. 2, the floor standing type five-axial C-arm holder unit has at an end (at the lower end in FIG. 7) of C-arm 71 an X-ray generating section 10 and at the other end (at the upper end in FIG. 7) of the C-arm 71 an X-ray detector 11, which are arranged oppositely to form an imaging system. A high-resolution detector 112 is fitted in front of the X-ray detector 111 by means of an arm mechanism 70. When the high-resolution detector 112 is not in use, it can be drawn back to a retreat position by means of a rotary mechanism arranged at the arm mechanism 70.

The C-arm 71 is held standing on a stand 73 by means of an arm holder 72. The C-arm 71 is fitted to a lateral side of the arm holder 72 so as to be able to slide in the direction of the axis of sliding rotation (axis of rotation Z1) as indicated by double arrow a. On the other hand, the arm holder 72 is fitted so as to be able to rotate around the horizontal axis of rotation (axis of rotation Z2) of the C-arm as indicated by double arrow b relative to the stand 73. Thus, as the arm holder 72 is driven to rotate, the C-arm 71 is also driven to rotate around the axis of rotation Z1.

The imaging system fitted to the opposite ends of the C-arm 71 is set to an arbitrarily selected angular position relative to the subject lying flat on the top plate by driving the C-arm 71 to slide in the a direction and also driving the arm holder 72 to rotate around the b direction. The imaging system is able to rotate around in the senses of C relative to the imaging axis (axis of rotation Z3). The intersection of the axis of rotation Z1, the axis of rotation Z2 and the axis of rotation Z3 is the center of rotation which is also referred to as isocenter IS. The image center line indicated by a dotted line in FIG. 7 is so defined as to pass through the isocenter IS.

On the other hand, floor swivel arm 74 is arranged on the floor surface 75 and one of the ends of the floor swivel arm 74 is fitted so as to be able to rotate around axis of rotation Z4 in the senses indicated by d relative to the floor surface 75. The stand 73 is fitted to the other end of the floor swivel arm 74 so as to be able to rotate around axis of rotation Z5 in the senses indicated by e. Note that both the axis of rotation Z4 of the floor swivel arm 74 and the axis of rotation Z5 of the stand 73 are set so as to extend in the direction of the Z-axis.

Thus, the floor standing type five-axial C-arm holder unit can be positionally controlled both in the longitudinal direction (the direction of the X-axis) and in the transversal direction (the direction of the Y-axis) relative to the subject P by driving the floor swivel arm 74 around the axis of rotation Z4 and also driving the stand 73 around axis of rotation Z5. Additionally, the relative angle between the imaging system and the subject can be adjusted by adjusting the axis of rotation Z3.

Thus, the defined values of the ROI can be moved to the center of the image obtained by means of the X-ray detector by controlling the rotary angles of the axes of rotation Z3, Z4, and Z5 relative to the differences of the coordinate values as calculated in Step ST406, which is described above for the first embodiment. In the case of rotational imaging such as 3D angio imaging, the height of the bed 13 is also controlled in order to make the center of the ROI accurately agree with the isocenter IS.

In this embodiment, the floor standing type five-axial C-arm holder unit is positionally adjusted in the longitudinal direction and also in the transversal direction by means of the axes of rotation Z3, Z4, and Z5. Therefore, the amount of move as illustrated in FIG. 5 is preferably displayed in terms of the angle of move of each of the axes of rotation in addition to the differences of the coordinate values of the X-axis, the Y-axis and the Z-axis. If such is the case, a graphical display may be provided to show the direction of move of the C-arm in addition to the angle of move of each of the axes of rotation so that the operator may intuitively comprehend the move of the C-arm.

With this embodiment again, when the subject P (patient) is made to bear an endoscope and/or a catheter, the operation of controlling the height of the top plate of the bed 13 can be manually performed as option for the sake of safety of the subject.

When the top plate of the bed 13 is provided with a control mechanism that can drive the top plate both in the longitudinal direction and in the transversal direction, advantages similar to the one described above for this embodiment can be obtained by moving the bed 13 instead of moving the C-arm of this embodiment. They can be obtained by way of a configuration same as the one illustrated in FIG. 1. However, when the subject (patient) is made to bear an endoscope and/or a catheter, preferably the C-arm is driven to move for the sake of safety of the subject.

Thus, the second embodiment that includes a floor standing type five-axial arm provides advantages similar to those of the first embodiment.

Third Embodiment

Figure 8:
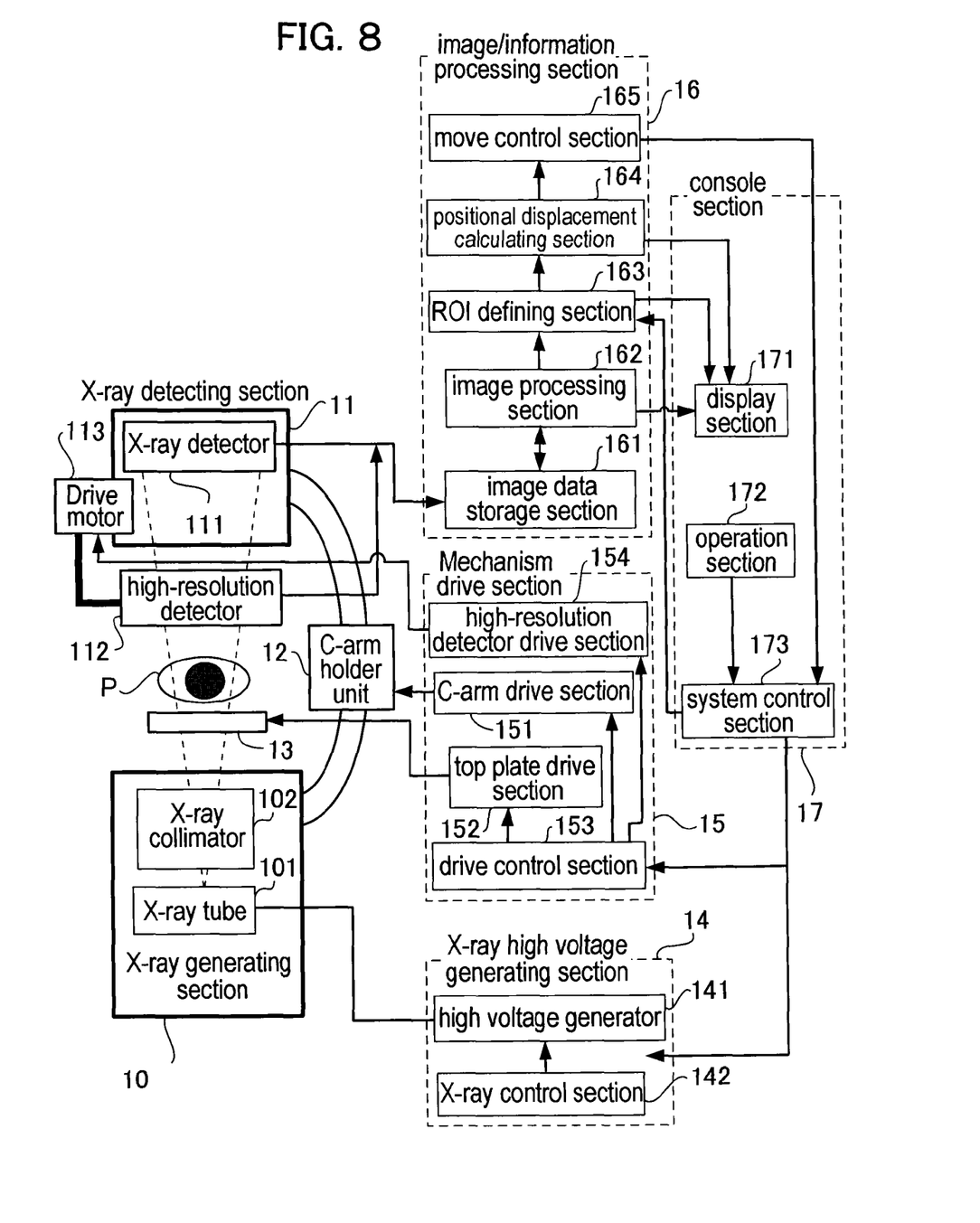
FIG. 8 is a schematic block diagram of X-ray image diagnosing apparatus according to a third embodiment of the present invention.

In the third embodiment, the high-resolution detector 112 can be automatically set in position and drawn away to a retreat position. FIG. 8 schematically illustrates the configuration of the X-ray image diagnosing apparatus of this embodiment. The X-ray image diagnosing apparatus of this embodiment differs from that of the apparatus illustrated in FIG. 1 in that a high-resolution detector drive section 154 is additionally arranged in the mechanism drive section 15 and a drive motor 113 that is controlled by the high-resolution detector drive section 154 is additionally arranged in the arm mechanism 70 for supporting the high-resolution detector 112.

Figure 9:
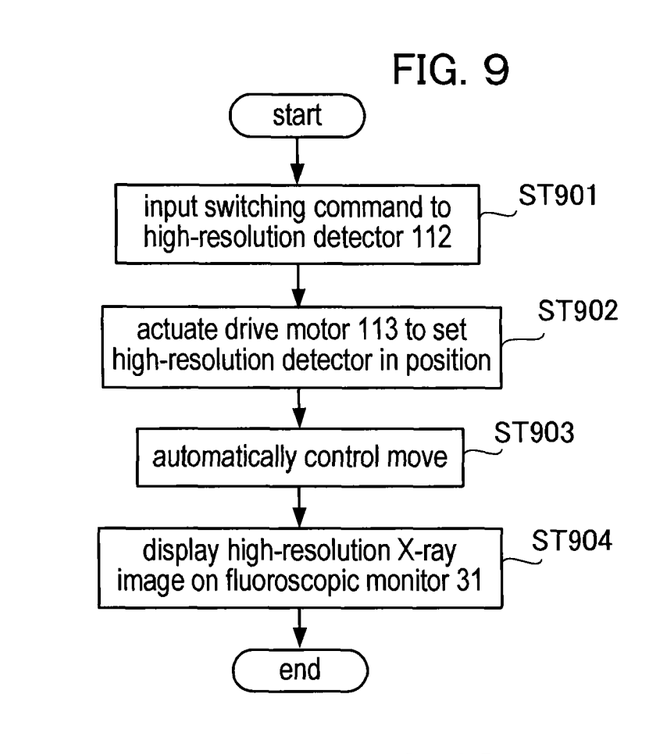
FIG. 9 is a flowchart of the automatic switching control operation for switching to the high-resolution detector of the third embodiment.

FIG. 9 is a flowchart of the automatically switching control operation for switching to the high-resolution detector 112. As shown in the flowchart, the high-resolution detector 112 is automatically set in position in front of the X-ray detector 111. This operation can conveniently be conducted along with the automatic move control operation described above for the first and second embodiments. More specifically, it may be so arranged that both the operation of setting the high-resolution detector 112 in position and that of automatically controlling the move of the defined ROI are executed simultaneously by depressing the automatic move button 54 shown in FIG. 5.

Alternatively, the operation of automatically setting the high-resolution detector 112 in front of the X-ray detector 111 may be conducted after the completion of the automatic move control operation.

In Step ST901, a switching command for switching to the high-resolution detector 112 is issued by means of the consol section 17. In Step ST902, the drive motor 113 is controlled by means of the switching command and the high-resolution detector 112 is set in position in front of the X-ray detector 111.

In Step ST903, an automatic move control operation is conducted for the defined ROI. Note that this step may be skipped when it is not necessary to conduct an automatic control operation. In Step ST904, a high-resolution X-ray image obtained by means of the high-resolution detector 112 is displayed on the fluoroscopic monitor 31.

Figure 10:
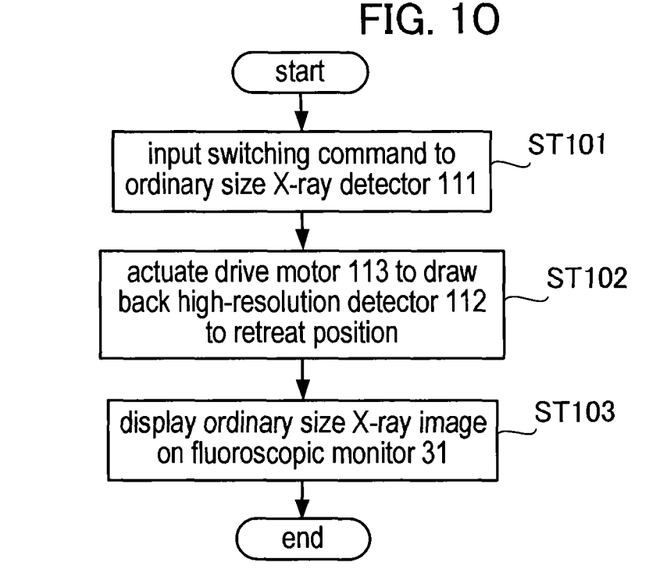
FIG. 10 is a flowchart of the automatic switching control operation for switching to the X-ray detector of the third embodiment.

FIG. 10 shows a flowchart of the automatic switching control operation for switching to the X-ray detector 111 having an ordinary visual field. The high-resolution detector 112 is automatically drawn away from the front side of the X-ray detector 111 according to the flowchart.

In Step ST101, a switching command for switching to the X-ray detector 111 is issued by means of the console section 17. In Step ST102, the drive motor 113 is controlled by means of the switching command and the high-resolution detector 112 is drawn away from the front side of the X-ray detector 111.

In Step ST103, the original image obtained by means of the X-ray detector 111 is redisplayed on the fluoroscopic monitor 31. Note that this step may be skipped when it is not necessary to redisplay the original image because the imaging conditions have been altered or for some other reason. Then, the operation ends when the high-resolution detector 112 is drawn away to the retreat position (Step ST102).

As described above, the high-resolution detector 112 of the third embodiment can automatically be set in position and then drawn away to a retreat position and this feature can be combined with the automatic move control feature. Thus, the third embodiment is very convenient for use and can be used to build a system having highly efficient manual procedures.

Thus, as described above by way of the preferred embodiments, an X-ray image diagnosing apparatus according to the present embodiment can display a ROI that corresponds to the small visual field of the high-resolution detector on an image of an ordinary size obtained by means of the X-ray detector and a ROI can be defined by means of a console. Additionally, an X-ray image diagnosing apparatus according to the present embodiment has a functional feature of causing the C-arm holder unit to operate as automatic follower and shift its position so as to move the ROI position to the center of the image obtained by means of the X-ray detector. This eliminates all the manual operations conventionally required for the doctor to select a compact high-resolution detector including a positioning operation. Thus, the third embodiment is very convenient for use and can be used to build a system having highly efficient manual procedures.

Additionally, this embodiment displays the direction (and the amount) of a move of its C-arm on a monitor before it starts an automatic follow-up operation. Thus, the operator is notified of the direction in which and the position to which the C-arm moves in advance. Then, any interference accident due to an unintended move of the C-arm can be prevented from taking place.

The present invention is by no means limited to the above-described embodiments, which may be modified and altered in various different ways without departing from the scope of the present invention. For example, the shape of the C-arm of each of the embodiments is described only as an example and the present invention is equally applicable to a biplane type C-arm. Furthermore, it is not necessary to use a C-arm. For the purpose of the present invention, an X-ray image may be a fluoroscopic image, a reconstructed 3D image such as a 3D-angio image, an image formed by means of oblique incident X-rays or some other image.

Thus, an X-ray image diagnosing apparatus according to the present embodiment can automatically display a high-resolution image of a ROI part obtained by means of the high-resolution detector at the center of an X-ray image that is obtained by means of the X-ray detector and being displayed on the X-ray image display screen. This eliminates all the manual operations conventionally required for the doctor to move a ROI to the center of an X-ray image being displayed on the display screen.

While certain embodiments have been described, these embodiments have been presented by way of example only, and are not intended to limit the scope of the inventions. Indeed, the novel embodiments described herein may be embodied in a variety of other forms; furthermore, various omissions, substitutions and change in the form of the embodiments described herein may be made without departing from the spirit of the invention. The accompanying claims and their equivalents are intended to cover such forms or modifications as would fall within the scope and split of the inventions.

What is claimed is:

1. An X-ray image diagnosing apparatus comprising:
    a top plate for laying a subject to be examined;
    an X-ray detecting section including an X-ray detector having a first visual field size and a high-resolution detector showing a resolution higher than the X-ray detector and having a second visual field size smaller than the visual field of the X-ray detector;
    an X-ray generating section for irradiating the subject with X-rays;
    a holding section for holding the X-ray detecting section and the X-ray generating section so as to make them face each other;
    an image processing section for generating a first X-ray image by means of the X-ray detector and a second X-ray image by means of the high-resolution detector;
    a display section for displaying the first X-ray image and the second X-ray image;
    a region defining section for displaying a spot corresponding to part of the second X-ray image or a region corresponding to the second X-ray image on the first X-ray image and specifying the position of the high-resolution detector by moving the spot or the region;
    a positional displacement calculating section for determining the coordinate difference between the center position of the first X-ray image and the position of the spot indicating the specified position of the high-resolution detector or a substantial center position of the region; and
    a move control section for controlling the top plate or the holding section so as to move the substantial center position of the second X-ray image to a substantial center of the image display region of the display section.

2. The X-ray image diagnosing apparatus according to claim 1, wherein the move control section controls the high-resolution detector in conjunction with an operation of controlling the top plate or the holding section.

3. The X-ray image diagnosing apparatus according to claim 2, further comprising:
    a support mechanism for supporting the high-resolution detector in front of the X-ray detector; and
    a retreat mechanism arranged in the support mechanism to allow the high-resolution detector to be drawn away from the front side of the X-ray detector.

4. The X-ray image diagnosing apparatus according to claim 3, further comprising a high-resolution detector drive section capable of switching from the X-ray detector to the high-resolution detector when retreating by the retreat mechanism.

5. The X-ray image diagnosing apparatus according to claim 4, wherein the coordinate difference calculated by the positional displacement calculating section can be displayed by the region specifying section.

6. The X-ray image diagnosing apparatus according to claim 5, further comprising a button for starting a move control operation by the move control section.

7. An X-ray image diagnosing apparatus comprising:
    an X-ray detecting section including an X-ray detector having a first visual field size and a high-resolution detector showing a resolution higher than the X-ray detector and having a second visual field size smaller than the visual field of the X-ray detector;
    an X-ray generating section for irradiating a subject with X-rays;
    a C-arm holding unit carrying an imaging system formed by an X-ray detecting section disposed oppositely relative to the X-ray generating section so as to be capable of rotating;
    a C-arm drive section for controlling the position of the C-arm holding unit;
    an image processing section for generating X-ray images of a subject by means of the X-ray detector and the high-resolution detector;
    a ROI defining section for displaying a marker corresponding to the second visual field size as a ROI defining image on the X-ray image of the first visual field size and defining the ROI by moving the marker to the ROI;
    a positional displacement calculating section for determining the coordinate difference between the center position of the X-ray image of the first visual field size and the center position of the marker; and
    a move control section for controlling an operation of moving the center position of the ROI substantially to the center of the X-ray image of the first visual field size according to the coordinate difference by controlling the C-arm drive section.

8. The X-ray image diagnosing apparatus according to claim 7, wherein the move control operation can be selectively executed by depressing a move button.

9. The X-ray image diagnosing apparatus according to claim 7, wherein the coordinate difference calculated by the positional displacement calculating section is further displayed in the ROI defining image.

10. The X-ray image diagnosing apparatus according to claim 9, wherein the move control operation can be selectively executed by depressing a move button.

11. An X-ray image diagnosing apparatus comprising:
    an X-ray detecting section including an X-ray detector having a first visual field size and a high-resolution detector showing a resolution higher than the X-ray detector and having a second visual field size smaller than the visual field of the X-ray detector;
    a C-arm holding unit carrying an X-ray generating section for irradiating a subject with X-rays and an imaging system formed by an X-ray detecting section disposed oppositely relative to the X-ray generating section so as to be capable of rotating;
    a bed arranged between the X-ray generating section and the X-ray detecting section;
    a C-arm drive section for controlling the position of the C-arm holding unit;
    a top plate drive section for controlling the position of the top plate of the bed;
    an image processing section for generating X-ray images of a subject by means of the X-ray detector and the high-resolution detector;
    a ROI defining section for displaying a marker corresponding to the second visual field size as a ROI defining image on an X-ray image of the first visual field size and defining the ROI by moving the marker to the ROI;

a positional displacement calculating section for determining the coordinate difference between the center position of the X-ray image of the first visual field size and the center position of the marker; and a move control section for controlling an operation of moving the center position of the ROI substantially to the center of the X-ray image of the first visual field size according to the coordinate difference by controlling the C-arm drive section and the top plate drive section.

12. The X-ray image diagnosing apparatus according to claim 11, wherein the coordinate difference calculated by the positional displacement calculating section is further displayed in the ROI defining image.

13. The X-ray image diagnosing apparatus according to claim 12, wherein the X-ray detector is an FPD.

14. The X-ray image diagnosing apparatus according to claim 13, further comprising:

a support mechanism for supporting the high-resolution detector in front of the X-ray detector; and a retreat mechanism arranged in the support mechanism to allow the high-resolution detector to be drawn away from the front side of the X-ray detector.

15. The X-ray image diagnosing apparatus according to claim 14, further comprising a high-resolution detector drive section capable of switching from the X-ray detector to the high-resolution detector by controlling a retreat mechanism arranged in the support mechanism at the time of controlling an operation of moving the center position of the X-ray image of the first visual field size to the center position of the ROI.

\* \* \* \* \*